United States Patent [19]
Oldham

[11] 4,064,883
[45] Dec. 27, 1977

[54] DENTAL FLOSS THREADER WITH LOCKING MEANS

[75] Inventor: George Ronald Oldham, Lakewood, N.J.

[73] Assignee: Johnson & Johnson, New Brunswick, N.J.

[21] Appl. No.: 682,282

[22] Filed: May 3, 1976

[51] Int. Cl.² ............................................. A61C 15/00
[52] U.S. Cl. ..................................................... 132/93
[58] Field of Search .................................. 132/82–93; 32/40 R

[56] References Cited
U.S. PATENT DOCUMENTS

| | | | |
|---|---|---|---|
| 3,650,392 | 3/1972 | Haagedoorn | 132/89 |
| 3,929,144 | 12/1975 | Tarrson | 132/93 |

*Primary Examiner*—Robert Peshock
*Attorney, Agent, or Firm*—Richard J. Rodrick

[57] ABSTRACT

A dental floss threader which is adapted to lock dental floss thereto. The threader includes a semi-rigid shank with smooth surfaces, and an eyelet attached to one end of the shank, the eyelet also being semi-rigid with smoothy surfaces. Associated with the eyelet is locking means responsive to insertion of dental floss therein for locking the dental floss to the threader.

3 Claims, 5 Drawing Figures

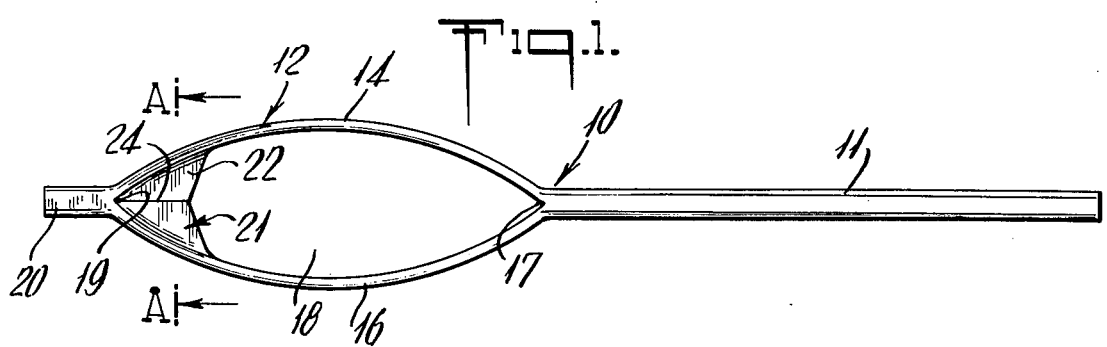
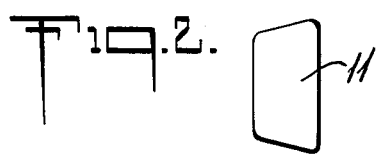
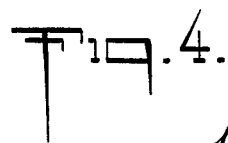
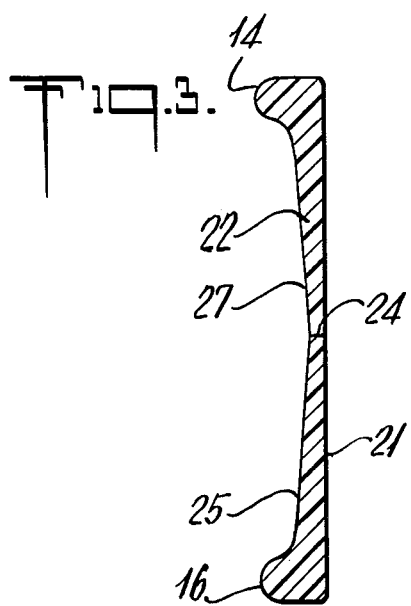
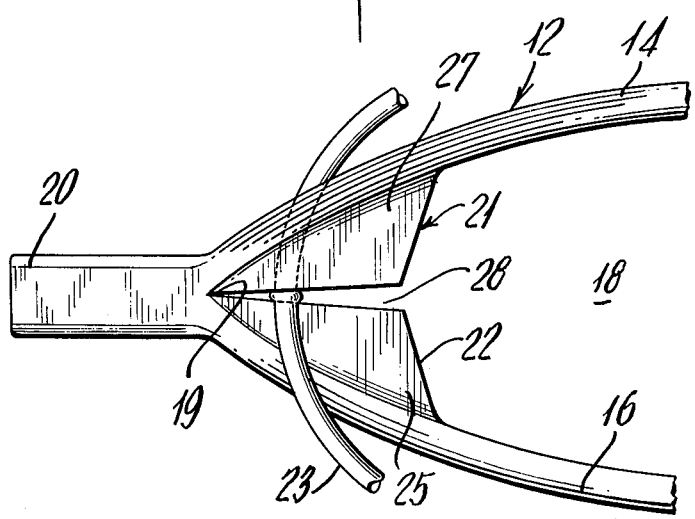
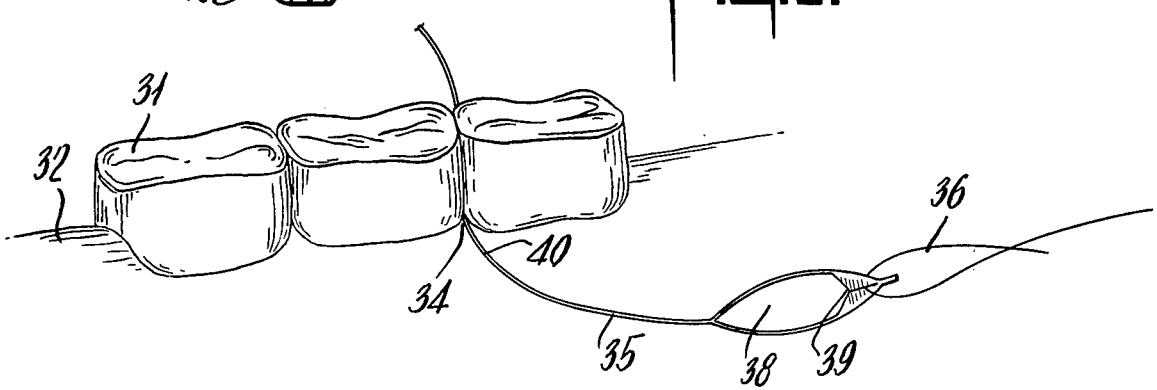

DENTAL FLOSS THREADER WITH LOCKING MEANS

BACKGROUND OF THE INVENTION

This invention relates generally to dental floss threaders, and more particularly concerns dental floss threaders used in conjunction with cleaning beneath fixed bridgework and difficult to reach areas within the mouth.

Dental floss is used to clean teeth, especially in those areas between teeth which cannot be reached by an ordinary toothbrush. In some areas of the mouth and in situations where fixed bridges and jacket crown are present it is often difficult, however, to slide and maneuver the dental floss into and under the area to be cleaned. The thread-like nature of most dental flosses produces this handling difficulty since the thread does not have the structure to be inserted in the hard to reach places.

One of the techniques to overcome this shortfall is the use of a threading device which threads the dental floss under the bridges and between crowns and the like. A number of threading devices are known and available to accomplish the insertion of dental floss into difficult areas in the mouth. Generally, the known dental floss threaders are needle-like in appearance, with a long, slender, usually flat shank portion with an eyelet, loop or "v" wedge at one end. These threaders are somewhat rigid in structure, but are smoothly surfaced so that they may be easily slipped and guided into the areas to be cleaned. To be used, dental floss is strung into the eyelet of the threader and looped therethrough; the threader then is inserted into the area to be cleaned, pulling the dental floss with it so that the floss can be used for its intended purpose.

It has been found that merely looping the dental floss in and around the eyelet often does not maintain the floss securely during use, and that slipping of the floss results. This and other deficiencies in the known dental floss threaders indicate that there is further need for improvement in this field.

SUMMARY OF THE INVENTION

The new dental floss threader of the present invention not only overcomes the inadequacies of prior floss threaders as explained above, but also offers other advantageous features as well. The primary advantage of this new dental floss threader lies in a locking feature which secures dental floss to the threader by merely inserting the floss in place with no tying required. When locking in place on the threader the dental floss is susceptible to little or no slippage during the threader insertion and subsequent cleaning functions, especially of bridgework and hard to reach areas.

Besides the locking feature the new dental floss threader is easily strung with the dental floss, is conveniently sized and disposable, and due to its flexibility, structure and smoothness, provides comfort to the user. Furthermore, certain and preferred embodiments of the new threader are molded in an integral structure which minimizes the expense of fabrication while keeping the cost of these threaders economical.

In accordance with the invention a dental floss threader has been discovered to which dental floss is locked so that the dental floss may be threaded under bridges, between jacket crowns and other areas with little or no slipping. This new threader has a semi-rigid shank with smooth surfaces, and an eyelet for receiving dental floss at one end of the shank. The eyelet is also comprised of smooth, semi-rigid material. Associated with the eyelet is locking means which is responsive to insertion of dental floss for locking the dental floss to the threader.

In the preferred embodiment of the new dental floss threader the shank, eyelet and locking means are formed of plastic material into an integral or unitary structure, with the locking means being integrally joined to the eyelet within the plane of the loop of the same. The eyelet of this embodiment is formed by a division of the shank at one end into two narrow filaments which diverge in arc-like fashion and then converge again at a distance from the end of the shank, thereby forming an elongated loop. Forming the locking means is a thin film of the plastic material integrally connected to the narrow filaments and extending from the point of convergence of the filaments a short distance into the plane of the eyelet. Between the converging filaments the thin film is capable of being separated so that when dental floss is inserted into the eyelet and is urged against the film, the film separates to form a slot. The dental floss settles into the slot where it is locked in place to prevent slipping during subsequent operations.

BRIEF DESCRIPTION OF THE DRAWINGS

These and other advantages, features and aspects of the invention will become apparent upon reading the following detailed description and upon reference to the accompanying drawings, in which:

FIG. 1 is a plan view the preferred embodiment of the new dental floss threader;

FIG. 2 is an end view of the threader of FIG. 1;

FIG. 3 is an enlarged sectional view taken along lines A—A of FIG. 1;

FIG. 4 is an enlarged plan view showing dental floss locked in place on the threader; and FIG. 5 is a perspective view showing a typical dental area to be cleaned by dental floss with the aid of the new dental floss threader.

While the invention will be described in connection with a preferred embodiment, it will be understood that it is not intended to limit the invention to that embodiment. On the contrary, it is intended to cover all alternatives, modifications and equivalents as may be included within the spirit and scope of the described invention.

DETAILED DESCRIPTION OF THE INVENTION

Adverting to the drawings wherein the preferred embodiment of the invention is depicted, there is shown a dental floss threader 10. The threader 10 has a semi-rigid shank portion 11 which has smooth surfaces and preferably has a smoothed-edge trapezoidal cross-section as seen in FIG. 2. Of course, other cross-sectional configurations such as semi-circular, rectangular and others may also conveniently be used. By semi-rigid is meant that the shank is capable of remaining substantially straight and somewhat stiff when no force is applied against or to the shank; however, the shank is also capable of being flexed, bent and curved under applied force so that the threader may be manipulated into difficult areas. Also by having smooth surfaces and edges the threader is more readily inserted and subsequently pulled through tight, difficult areas between teeth and/or crowns. To provide handling ease the shank 11 normally has a length of 1 to 4 inches (2.54 to 10.2 cm.) so that the threader may be manipulated properly; however, when desirable, or where length of the shank is not critical, shank lengths may be shorter or longer depending upon choice.

At one end of the shank 11 is an eyelet 12 or loop which, in this embodiment, is integrally joined to the shank 11, and, of course, is formed of the same type material as shank 11. The eyelet 12 is formed by a division of the shank material at one end into two filaments 14 and 16. Since the filaments 14 and 16 are divided portions of the shank, the cross-sectional areas of each filament are less than the cross-sectional area of the shank 11. The filaments, as the shank, also are comprised of semi-rigid material, preferably having flat faces. As the filaments separate at the point of divergence 17 they form opposing arcs with a loop 18 resulting between the arcing filaments 14 and 16. At a point 19 spaced a distance from the end of the shank at the point of divergence 17, the filaments 14 and 16 converge to form an elongated loop 18. The elongated loop provides an eyelet which is easily threaded with dental floss. Where the filaments integrally join together again at the point of convergence 19 they form a short, unitary stem 20. The stem 20 resembles the shank 11 in cross-sectional appearance, but is much smaller in length, in the range of a small fraction on an inch, sufficiently long to allow the two filaments to merge into an integral structure at that end of the eyelet 12.

Associated with the eyelet 12 is locking means 21 which is responsive to insertion of dental floss for locking the dental floss to the threader. Referring to FIGS. 3 and 4, in particular, the preferred locking means 21 is integrally joined to the eyelet 12 within the plane of the loop 18 formed by the arcing filaments 14 and 16. Of course, when integrally joined, the locking means 21 is the same type of material as the filaments of the eyelet. The locking means, in the embodiment shown and being described, consists of a film 22 of material, in this instance, plastic, which extends from the point of convergence 19 of the filaments a short distance into the plane of the loop 18 of the eyelet 12. As seen in FIGS. 1 and 3 the film 22 connects the converging filaments 14 and 16 as they approach the converging point 19. It is also evident, especially in FIG. 3, that the film 22 has a thickness which is less than the thickness of the filaments 14 and 16.

In one embodiment of the locking means the film 22 is perforated or weakened at a point 24 near the center of the film, the perforation extending to the point of convergence 19. When dental floss 23 is urged against the film 22 in the vicinity of the weakened area, the film separates into two portions 25 and 27 with a slot 28 formed between those portions which entends into the point of convergence 19. With the dental floss 23 being urged into the slot 28, the separated film portions 25 and 27 and the slot 28 cooperate to lock the floss in place to prevent it from slipping during use. As clearly seen in FIG. 4 the film portions 25 and 27 squeeze or pinch the dental floss in the slot so that the floss is firmly gripped and is subject to little or virtually no relative movement while in the eyelet. In other words, the dental floss is locked in its inserted position.

In another embodiment instead of perforated or weakened areas 24 near the center of the film 22 a slot 28 may be included in the film before the dental floss is inserted. The slot 28 is knife-like in appearance extending into the point of conveyence 19, sufficiently narrow so that the separated film portions 25 and 27 remain in virtual contact with each other. When the dental floss 23 is inserted into the eyelet, and urged against the film 22, it merely separates the two portions 25 and 27 and becomes lodged and locked in the slot 28 between those portions.

In a further embodiment, to assure superior locking strength the slot surfaces of the film portions 25 and 27 are textured or roughened so that the dental floss will be further prevented from slipping during use.

While a number of different materials may be selected to combine the properties of semi-rigidity and smooth surfaces with resulting ease of and comfort during use, plastic materials are the most desirable. For instance, a threader made of nylon may be readily fabricated so that the shank, the eyelet and the looking means are integrally joined in the respective positions on the threader. Especially when the locking means is a thin film of material does plastic lend itself to the threader construction since the film is merely a flattened portion of plastic between the filaments in the area of convergence. Furthermore, plastic materials, such as nylon, polyolefin, acetal and the like, may be injection molded so that the threader may be fabricated as one integral, unitary structure, with no subsequent heating or adhesive operations required to unitize the components of the threader.

As mentioned above the shank of the threader normally has a length of from 1 to 4 inches (2.54 to 10.2 cm), but the length of the shank may vary according to choice or specific adaptation. In the preferred embodiment, when the shank is about 1¾ inches (4.45 cm) long, the eyelet, from points of divergence to convergence, is about 1 inch (2.54 cm) in length, with the stem being approximately ⅛ inch (0.318 cm) long, for an overall length of the threader of about 2 7/8 inches (7.30 cm). The eyelet has an opening across its maximum width of slightly less than ¼ inch (0.636 cm), but this distance may change according to whatever size is desired, compatible with the material being used and the expected specific function of the threader.

It has been found that the threaders having rounded edges, as seen especially in FIG. 2, provide comfort during use since the rounded portions more easily slide into the difficult to clean areas. Accordingly, typical threaders of this invention have shank portions with widths between 0.020 and 0.040 inches (0.051 and 0.102 cm) and thickness between 0.010 and 0.020 inches (0.025 and 0.051 cm). The shank is generally divided widthwise into filaments so that typical filaments have widths approximately half the width of the shank, while the thickness of the filaments and the shank are all substantially equal.

On the other hand, the thickness of the thin film locking areas of the threader is much smaller than the filaments or the shank. For example, the film typically has a thickness between 0.0005 and 0.008 inches (0.0013 and 0.0203 cm). However, the cross-section of the film portion often is not, and need not be, constant throughout. Referring to FIG. 3 it is seen that the film tapers in cross-section so that the portion of the film immediately adjacent each filament is thicker in cross-section than at the center portion of the film. Moreover, the film also tapers to a fine feather edge as it extends away from the point of convergence 19.

Use of the new threader is depicted in FIG. 5. A bridge 31 is located in position, fixed within the mouth 32. To clean under the bridge such as designated at point 34, a new dental threader 35 is used with dental floss 36 attached thereto. The dental floss 36 is threaded through the eyelet 38 and is locked into place by the locking means 39 located within the eyelet 8. Shank portion 40 of the threader is inserted under the portion of the bridge to be cleaned and is pulled through. As the eyelet 38 passed under the bridge, the filaments forming the eyelet are compressed so that the eyelet may pass under. Once the eyelet passes the area to be cleaned the dental floss is now in proper position to perform its cleaning function. With the locking means associated with the eyelet the dental floss is securely locked in place so that it may be pulled into position by the threader without slippage, and may be used in conjunction with the threader without slipping.

Thus, it is apparent that there has been provided, in accordance with the invention, a new dental floss threader with locking means that fully satisfies the aims, advantages and aspects set forth above. While the invention has been described in conjunction with specific embodiments thereof, it is evident that many alternatives, modifications, and variations will be apparent to those skilled in the art in view of the foregoing description. Accordingly, the plenary invention is intended to embrace all such alternatives, modifications and variations as fall within the spirit and broad scope of the described invention.

What is claimed is:

1. A dental floss threader adapted to lock dental floss thereto comprising a semi-rigid shank having smooth surfaces; an eyelet integrally joined at one end of said shank, said eyelet being formed by a division at one end of said shank into two filaments, each filament having a cross sectional area less than the cross sectional area of said shank, said filaments diverging in arcuate opposing relationship and converging at a point spaced from said end of said shank thereby forming an elongated loop, said filaments being integrally merged at the point of convergence to form a short, unitary stem at that end of said eyelet; and locking means integrally joined to said eyelet and responsive to insertion of dental floss therein for locking said dental floss to said threader, said locking means and said eyelet being formed from plastic material, the locking means consisting of a film of plastic material extending from said point of convergence of the filaments a short distance into the plan of the eyelet so that the film connects the converging filaments, said film having a thickness less than the thickness of said filaments, said film being separable between said converging filaments so that when dental floss is inserted into said eyelet, and is urged against said film, said film separates to form a slot therein whereby said slot and separated film portions cooperate to lock said floss in place to prevent slippage of said floss during use.

2. A dental floss threader as defined in claim 1 wherein said film includes a slot near the center thereof extending into said point of convergence of the filaments thereby separating the film into two portions.

3. A dental floss threader as defined in claim 1 wherein the slot surfaces of the separated film portions are textured for greater locking strength of the inserted dental floss.

* * * * *

UNITED STATES PATENT AND TRADEMARK OFFICE
CERTIFICATE OF CORRECTION

PATENT NO. : 4,064,883
DATED : December 27, 1977
INVENTOR(S) : George Ronald Oldham It is certified that error appears in the above-identified patent and that said Letters Patent are hereby corrected as shown below:

In Abstract, line 5, "smoothy" should read ---smooth---
In Column 1, line 52, "locking in place" should read
 ---locked in place---
In Column 4, line 17, "looking means" should read
 ---locking means---
In Column 5, line 5, "eyelet 8" should read ---eyelet 38---
In Column 5, line 8, "passed under" should read
 ---passes under---
In Column 5, line 11, "dental floss is" should read
 ---dental floss 36 is---

Signed and Sealed this

Tenth Day of October 1978

[SEAL]

Attest:

RUTH C. MASON
*Attesting Officer*

DONALD W. BANNER
*Commissioner of Patents and Trademarks*